United States Patent [19]

Mertens et al.

[11] Patent Number: 4,810,801

[45] Date of Patent: Mar. 7, 1989

[54] PYRROLOBENZIMIDAZOLES, PHARMACEUTICAL COMPOSITIONS CONTAINING THEM, AND USE OF THEM TO TREAT CERTAIN HEART AND CIRCULATORY DISEASES

[75] Inventors: Alfred Mertens, Schriesheim; Jens-Peter Hölck, Mannheim; Wolfgang Kampe, Heddesheim; Bernd Müller-Beckmann, Grunstadt; Klaus Strein, Hemsbach; Wolfgang Schaumann, Heidelberg, all of Fed. Rep. of Germany

[73] Assignee: Boehringer Mannheim GmbH, Mannheim, Fed. Rep. of Germany

[21] Appl. No.: 103,895

[22] Filed: Oct. 1, 1987

Related U.S. Application Data

[63] Continuation-in-part of Ser. No. 807,260, Dec. 10, 1985.

[30] Foreign Application Priority Data

Dec. 14, 1984 [DE] Fed. Rep. of Germany ....... 3445699

[51] Int. Cl.$^4$ ................. C07D 209/54; C07D 405/12; C07D 211/22; C07D 413/12
[52] U.S. Cl. ..................................... 548/411; 548/336; 548/486; 540/543; 540/602; 544/70; 544/144; 546/15; 546/201

[58] Field of Search ............... 540/602, 543; 544/144, 544/70; 546/201, 15; 548/336, 486, 411

[56] References Cited

U.S. PATENT DOCUMENTS 4,234,571 11/1980 Nestor et al. ...................... 548/344

Primary Examiner—Mary C. Lee
Assistant Examiner—J. Richter
Attorney, Agent, or Firm—Felfe & Lynch

[57] ABSTRACT

The present invention provides new pyrrolobenzimidazoles of the general formula:

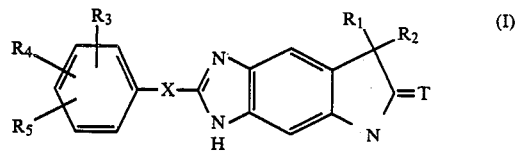

wherein $R_1$–$R_5$, X and T are as defined in the specification.

The present invention also provides processes for the preparation of these compounds and pharmaceuticals containing them for the prophylaxis and treatment of heart and circulatory diseases.

18 Claims, No Drawings

PYRROLOBENZIMIDAZOLES, PHARMACEUTICAL COMPOSITIONS CONTAINING THEM, AND USE OF THEM TO TREAT CERTAIN HEART AND CIRCULATORY DISEASES

This application is a continuation in part of Ser. No. 807,260, filed Dec. 10, 1985.

The present invention is concerned with new pyrrolobenzimidazoles, processes for the preparation thereof and pharmaceutical compositions containing them.

The new pyrrolobenzimidazoles according to the present invention are compounds of the general formula:

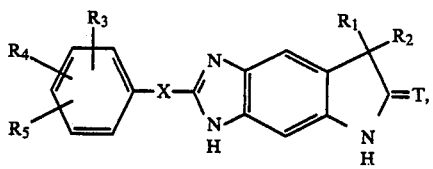

in which $R_1$ is a hydrogen atom or an alkyl, alkenyl or cycloalkyl radical; $R_2$ is a hydrogen atom or an alkyl, alkenyl or cyano group or a carbonyl group substituted by a hydroxyl, alkyl, alkoxy, amino, alkylamino, dialkylamino or hydrazino group or, together with $R_1$, represents a cycloalkylene radical or $R_1$ and $R_2$ together form an alkylidene or cycloalkylidene radical; $R_3$, $R_4$ and $R_5$, which can be the same or different, are hydrogen atoms, alkanesulphonyloxy, trifluoromethanesulphonyloxy, alkanesulphonylamino, trifluoromethanesulphonylamino, N-alkyl-alkanesulphonylamino, N-alkyl-trifluoromethanesulphonylamino, alkylsulphenylmethyl, alkylsulphinylmethyl or alkylsulphonylmethyl radicals, carbonyl groups substituted by a hydroxyl, alkoxy, amino, alkylamino or dialkylamino group, sulphonyl groups substituted by an amino, alkylamino, dialkylamino or cyclic imino group, whereby a methylene group in the 4-position of the so formed heterocycle can be replaced by a sulphur or oxygen atom, alkylcarbonylamino, aminocarbonylamino or alkylaminocarbonylamino radicals, alkylthio, alkylsulphinyl or alkylsulphonyl radicals, halogen atoms, nitro, amino, hydroxyl or cyano groups or alkyl, trifluoromethyl, alkoxy, alkenyloxy, alkynyloxy, cyanoalkoxy, carboxyalkoxy, alkoxycarbonylalkoxy, dialkylamino, 1-imidazolyl radicals; X is a valency bond, a $C_1$-$C_4$ alkylene radical or a vinyl radical and T is an oxygen or sulphur atom; as well as the tautomers thereof and the physiologically acceptable salts thereof with inorganic and organic acids.

Since, when $R_1$ is not the same as $R_2$, the compounds of general formula (I) possess an asymmetric carbon atom, the present invention also includes the optically-active forms and the racemic mixtures of these compounds.

The new compounds according to the present invention have valuable pharmacological properties and, in particular, they increase the strength of the heart and/or have a blood pressure-lowering action and/or influence the thrombocyte function and improve the microcirculation.

In general formula (I), the substituent $R_1$ represents hydrogen atom, an alkyl, cycloalkyl or alkenyl radical and $R_2$ represents a hydrogen atom, an alkyl or alkenyl radical, cyano group or carbonyl group substituted by a hydroxyl, alkyl, alkoxy, amino, alkylamino, dialkylamino or hydrazino group, in which the above-mentioned alkyl and alkenyl moieties can be straight-chained or branched and contain 1 to 6 or 2 to 6 carbon atoms, respectively, and the above-mentioned cycloalkyl moiety contains 3 to 7 carbon atoms.

$R_1$ is preferably a hydrogen atom or a methyl, ethyl, isopropyl, 3-pentyl, allyl, cyclopentyl or cyclohexyl radical and $R_2$ represents preferably a hydrogen atom or a methyl, ethyl, isopropyl, 3-pentyl, allyl, cyano, carboxyl, acetyl, propionyl, methoxycarbonyl, ethoxycarbonyl, aminocarbonyl, methylaminocarbonyl, dimethylaminocarbonyl or hydrazinocarbonyl radical.

$R_1$ and $R_2$, together with the carbon atom to which they are attached, can also form a cycloalkyl ring containing 3 to 7 carbon atoms, preferably a spirocyclopropyl, spirocyclobutyl, spirocyclopentyl or spirocyclohexyl radical.

$R_1$ and $R_2$ can together also form a $C_3$-$C_7$ alkylidene or $C_3$-$C_7$-cycloalkylidene radical, preferably an isopropylidene or cyclohexylidene radical.

The alkyl moiety of the substituents mentioned in the case of the definitions of $R_3$, $R_4$ and $R_5$ can contain up to 5 and preferably up to 4 carbon atoms. Thus, preferred examples of such substituents include methanesulphonyloxy, ethanesulphonyloxy, n-propanesulphonyloxy, isopropanesulphonyloxy, trifluoromethanesulphonyloxy, methylsulphenylmethyl, ethylsulphenylmethyl, n-propylsulphenylmethyl, methylsulphinylmethyl, ethylsulphinylmethyl, methylsulphonylmethyl, ethylsulphonylmethyl, n-propylsulphonylmethyl, methanesulphonylamino, ethanesulphonylamino, n-propanesulphonylamino, trifluoromethanesulphonylamino, N-methyl-methanesulphonylamino, N-ethyl-methanesulphonylamino, N-methyl-ethanesulphonylamino, N-ethyl-ethanesulphonylamino, N-isopropyl-ethanesulphonylamino, N-methyl-n-propanesulphonylamino, N-n-propyl-n-propanesulphonylamino, N-methyl-trifluoromethanesulphonylamino, N-ethyl-trifluoromethanesulphonylamino, N-isopropyltrifluoromethanesulphonylamino, methoxycarbonyl, ethoxycarbonyl, propoxycarbonyl, isopropoxycarbonyl, methylaminocarbonyl, ethylaminocarbonyl, dimethylaminocarbonyl, di-n-propylaminocarbonyl, N-methyl-ethylaminocarbonyl, methylaminosulphonyl, ethylaminosulphonyl, n-propylaminosulphonyl, n-butylaminosulphonyl, n-pentylaminosulphonyl, dimethylaminosulphonyl, diethylaminosulphonyl, di-n-propylaminosulphonyl, N-methyl-isopropylaminosulphonyl, acetylamino, propionylamino, methylaminocarbonylamino, ethylaminocarbonylamino, propylaminocarbonyl amino groups, methyl, ethyl, propyl, trifluoromethyl, methoxy, ethoxy, propoxy groups, allyloxy, but-2-enyloxy, but-3-enyloxy, pent-2-enyloxy, propargyloxy, but-2-ynyloxy, but-3-ynyloxy, cyanomethoxy, cyanoethoxy, methoxycarbonylmethoxy, methoxycarbonylethoxy, methylthio, ethylthio, methylsulphinyl, ethylsulphinyl, methylsulphonyl and ethylsulphonyl groups.

Sulphonyl groups which can be substituted by cyclic imino groups are preferably morpholino-, pyrrolidino-, piperidino- and hexamethyleneiminosulphonyl groups.

In particular, $R_3$ can be, for example, a hydrogen atom, an alkylsulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radical, a carbonyl group substituted by a hydroxy, alkoxy, amino, alkylamino or dialkylamino group or a sulphonyl group substituted by an amino, dialkylamino or morpholino group, whereby each of the above-mentioned alkyl moieties can contain 1 or 2 carbon atoms, a nitro, cyano or alkylaminosulphonyl group with up to 4 carbon atoms, an alkylcarbonylamino, aminocarbonylamino or N-alkyl-aminocarbonylamino group, an alkylthio, alkylsulphinyl or alkylsulphonyl group, whereby each of the above-mentioned alkyl moieties can contain 1 or 2 carbon atoms, a halogen, amino, hydroxyl, dialkylamino, alkyl, trifluoromethyl, alkoxy, alkenyloxy or alkynyloxy group preferably with up to 3 carbon atoms, a cyanomethoxy, methoxycarbonylmethoxy or imidazolyl radical; $R_4$ can be, for example, a hydrogen atom, an alkyl radical containing up to 3 carbon atoms, an alkoxy or dialkylamino radical with 1 or 2 carbon atoms in each alkyl moiety or a halogen atom; and $R_5$ can be, for example, a hydrogen atom or a methoxy radical.

The phenyl moiety can carry 1 to 3 of the mentioned substituents.

Preferred monosubstituted compounds include the hydroxyl, $C_1$-$C_3$-alkyl, trifluoromethyl, $C_1$-$C_3$-alkoxy, allyloxy, propargyloxy, cyanomethoxy, methoxycarbonylmethoxy, halogeno, nitro, amino, $C_1$-$C_3$-dialkylamino, $C_1$-$C_3$-alkylthio, $C_1$-$C_3$-alkylsulphinyl, $C_1$-$C_3$-alkylsulphonyl, $C_1$-$C_3$-alkylsulphonyloxy and the 1-imidazolyl compounds, whereby the substituent can be in the 2-, 3- or 4-position.

Preferred disubstituted compounds contain, as substituents, an alkanesulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radical, a carbonyl group substituted by a hydroxyl, alkoxy, amino, alkylamino or dialkylamino group or a sulphonyl group substituted by an amino, dialkylamino or morpholino group, an alkylaminosulphonyl, alkylcarbonylamino, aminocarbonylamino or N-alkyl-aminocarbonylamino group, a hydroxyl, alkyl, trifluoromethyl, alkoxy, allyloxy, propargyloxy, cyanomethoxy, methoxycarbonylmethoxy, cyano, halogeno, nitro, amino, dialkylamino, alkylthio, alkylsulphinyl, alkylsulphonyl or an 1-imidazolyl group, whereby the two substituents can be the same or different and can be in the 2,3-, 2,4-, 2,5-, 2,6- 3,4- or 3,5-position but preferably in the 2,4-, 2,5- or 3,4-position and the above-mentioned alkyl radical, alone or in combination with other radicals, can contain up to 3 carbon atoms.

A preferred trisubstituted phenyl radical is the 3,4,5-trimethoxyphenyl radical.

X is preferably a valency bond or a methylene, ethylene or vinyl radical and T is preferably an oxygen or sulphur atom.

Especially preferred compounds of general formula (I) are those in which $R_1$ represents a hydrogen atom, methyl or ethyl radical and $R_2$ represents methyl, ethyl, isopropyl, cyano, acetyl, methoxycarbonyl, ethoxycarbonyl, aminocarbonyl or hydrazinocarbonyl; or $R_1$ and $R_2$ together represent a spirocyclopentyl ring when $R_1$ and $R_2$, together with the carbon atom to which they are attached, form a cycloalkyl ring; $R_3$ is hydrogen, methanesulphonyloxy, trifluoromethanesulphonyloxy, methanesulphonylamino, trifluoromethanesulphonylamino, methanesulphonylmethylamino, trifluoromethanesulphonylmethylamino, methylsulphenylmethyl, methylsulphinylmethyl, methylsulphonylmethyl, aminocarbonyl, aminosulphonyl, methylaminosulphonyl, dimethylaminosulphonyl, acetylamino, methythio, methylsulphonyl, hydroxyl, methyl, methoxy, propargyloxy, cyanomethoxy, methoxycarbonylmethoxy, cyano, chloro, nitro, amino, dimethylamino or 1-imidazolyl; $R_4$ is hydrogen, methyl, methoxy, dimethylamino or chloro; $R_5$ is hydrogen or methoxy; X is a valency bond, an alkylene radical containing 1 or 2 carbon atoms or a vinyl radical; and T is an oxygen atom.

The new compounds of general formula (I) according to the present invention can be prepared, for example, in one of the following ways:

(a) Reaction of a compound of the general formula:

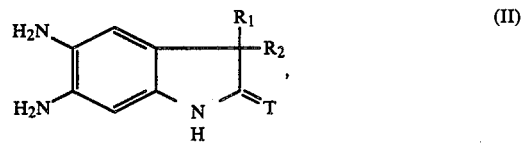

in which $R_1$, $R_2$ and T have the above-given meanings, with a compound of the general formula:

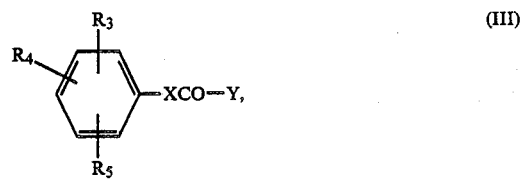

in which $R_3$, $R_4$, $R_5$ and X have the above-given meanings and Y is either a hydrogen atom or a residue which is easily split off, and the compound obtained is cyclised to give a compound of general formula (I) or a tautomer thereof and the compound obtained of general formula (I) according to the present invention is, if desired, converted into another compound of general formula (I) or a tautomer thereof and/or a compound obtained of general formula (I) or a tautomer thereof is, if desired, converted into a physiologically acceptable acid addition salt with an inorganic or organic acid.

Compounds of general formula (II) are the subject of Federal Republic of German Patent Specification No. P 34 17 643.8. New compounds can be prepared by the processes described therein.

The compounds of general formula (III) are preferably aldehydes, as well as acid halides, such as acid chlorides, carboxylic acid esters, such as methyl and ethyl esters, and other activated carboxylic acid derivatives, for example anhydrides.

If the compound of general formula (III) is an aldehyde, the reaction to give a Schiff base with a compound of general formula (II) preferably takes place in an alcoholic medium and the subsequent cyclisation and oxidation to give a compound of general formula (I) takes place by heating the reaction mixture to reflux temperature in the presence of atmospheric oxygen and a catalytic amount of an acid, for example, toluenesulphonic acid.

If the compound of general formula (III) is a carboxylic acid derivative, the reaction with a compound of general formula (II) to give an amide takes place in an inert solvent, preferably in methylene chloride, and the subsequent cyclisation to give a compound of general formula (I) is carried out in an acidic medium, preferably in the presence of a mineral acid, such as sulphuric acid or hydrochloric acid, in alcoholic solution.

(b) Acylation of a compound of the general formula:

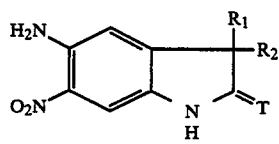
(IV)

or

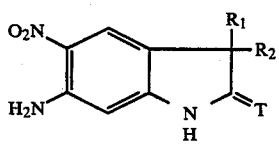
(V)

in which $R_1$, $R_2$ and T have the above-given meanings, with a compound of general formula (III), in which $R_3$, $R_4$, $R_5$ and X have the above-given meanings and Y is a residue which is easily split off, using processes which are known from the literature, to give a compound of the general formula:

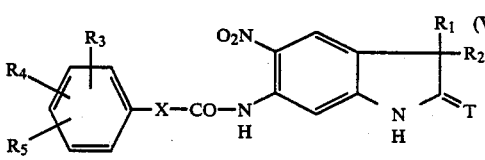
(VI)

or of the general formula:

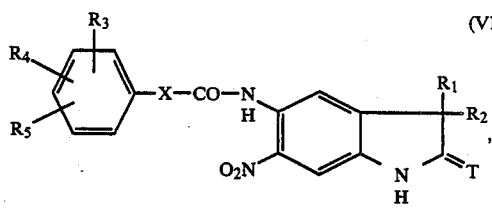
(VII)

in which $R_1$, $R_2$, $R_3$, $R_4$, $R_5$, X and T have the above-given meanings, which after hydrogenation and cyclisation gives a compound of general formula (I).

(c) Starting from a compound of the general formula:

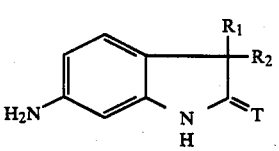
(VIII)

or

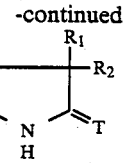
(IX)

in which $R_1$, $R_2$ and T have the above-given meanings, by reaction with a compound of general formula (III), in which Y is a residue which is easily split off, there is obtained, in known manner, a compound of the general formula:

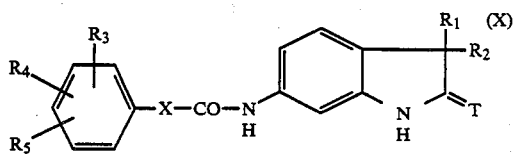
(X)

or of the general formula:

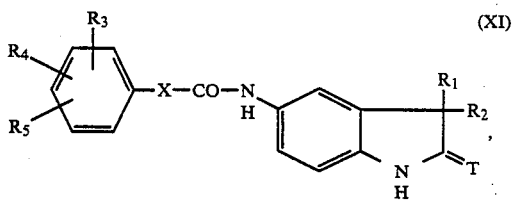
(XI)

in which $R_1$, $R_2$, $R_3$, $R_4$, $R_5$, T and X have the above-given meanings, which, in known manner, is converted by nitration into a compound of the general formula:

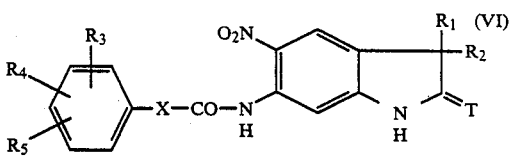
(VI)

or of the general formula:

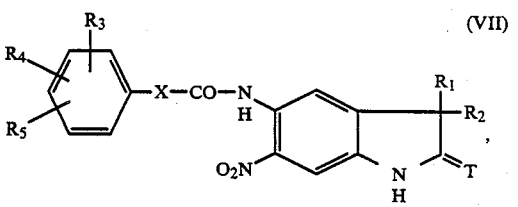
(VII)

in which $R_1$, $R_2$, $R_3$, $R_4$, $R_5$, T and X have the above-given meanings.

After hydrogenation of the nitro group in the compound of general formula (VI) or (VII) to give the corresponding amino compound, this is cyclised to give the desired compound of general formula (I).

The compounds of general formulae (II), (IV), (V), (VIII) and (IX) are the subject matter of Federal Republic of Germany Patent Specification No. P 34 17 643.8. New compounds can be prepared by the processes described therein.

The compounds of general formula (III) are to be understood to be especially acid halides, for example acid chlorides, or carboxylic acid esters or other activated carboxylic acid derivatives, for example anhydrides.

The reaction to give compounds of general formulae (VI) and (VII) is preferably carried out in an inert solvent at a temperature of from 0° C. to the boiling point of the solvent used, optionally with the addition of an adjuvant base, for example triethylamine or pyridine.

The hydrogenation of compounds of the general formulae (VI) and (VII) is preferably carried out in a solvent, for example water, water/ethanol, methanol, glacial acetic acid, ethyl acetate or dimethylformamide, preferably with hydrogen in the presence of a hydrogenation catalyst, such as Raney nickel, platinum or palladium/charcoal, with metals, such as iron, tin or zinc in the presence of an acid, with salts, such as ferrous sulphate, stannous chloride, sodium sulphide, sodium hydrogen sulphide or sodium dithionite, or with hydrazine in the presence of Raney nickel at a temperature of from 0° to 50° C. but preferably at ambient temperature.

The cyclisation of the so-obtained 5-amino or 6-amino-indoline-2-one derivatives is preferably carried out in a solvent or solvent mixture, such as ethanol, isopropanol, glacial acetic acid, benzene, chlorobenzene, toluene, xylene, glycol, glycol monomethyl ether, sulpholane, dimethylformamide or tetraline, at a temperature of from 0° to 250° C. but preferably at the boiling temperature of the reaction mixture, possibly in the presence of a condensation agent, such as sulphuric acid, p-toluenesulphonic acid, hydrochloric acid, phosphoric acid, polyphosphoric acid, acetic anhydride or possibly also in the presence of a base, such as potassium methylate or potassium tert.-butylate. However, the cyclisation can also be carried out without a solvent and/or condensation agent.

A compound of general formula (I), in which $R_1$ and $R_2$ are both hydrogen atoms, can subsequently be converted into another compound of general formula (I). This concerns also, for example, the reaction with compounds of the general formula:

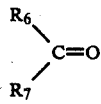

(XII)

in which $R_6$ and $R_7$ are alkyl radicals or $R_6$ together with $R_7$ forms a $C_3$-$C_7$ cycloalkylene radical, in the presence of a base, such as ammonia or triethylamine, in alcoholic solution. In particular, this concerns compounds of general formula (I), in which $R_1$ and $R_2$ are both hydrogen atoms, to give compounds in which $R_1$ together with $R_2$ represents a isopropylidene cyclopentylidene or cyclohexylidene radical, as well as possibly the hydrogenation thereof to give corresponding compounds of general formula (I), in which $R_1$ or $R_2$ is hydrogen.

The preparation of compounds of general formula (I), in which $R_3$ is an alkylsulphinyl, alkylsulphonyl, alkylsulphinylmethyl or alkylsulphonylmethyl radical, can be achieved by the subsequent oxidation of a compound of the general formula:

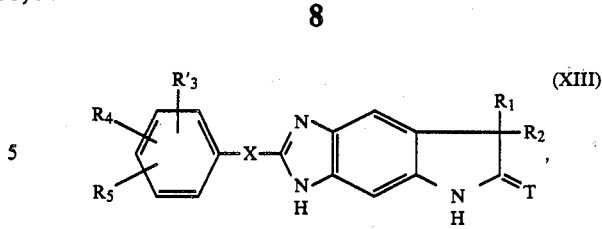

(XIII)

in which $R_1$, $R_2$, $R_4$, $R_5$, X and T have the above-given meanings and $R'_3$ is an alkylthio or alkylsulphenylmethyl radical with, in each case, up to 3 carbon atoms in the alkyl moiety.

The oxidation is preferably carried out in a solvent or solvent mixture, for example in water, water/pyridine, acetone, glacial acetic acid, dilute sulphuric acid or trifluoroacetic acid, at a temperature of preferably from −80° to 100° C., depending upon the oxidation agent used.

For the preparation of an alkylsulphinyl or alkylsulphinylmethyl compound of general formula (I), the oxidation is preferably carried out with one equivalent of the oxidation agent employed, for example, with hydrogen peroxide in glacial acetic acid, trifluoroacetic acid or formic acid at 0° to 20° C. or in acetone at 0° to 60° C., with a per acid, such as performic acid in glacial acetic acid or trifluoroacetic acid 0° to 50° C. or with m-chloroperbenzoic acid in methylene chloride or chdloroform at −20° to 60° C., with sodium metaperiodate in aqueous methanol or ethanol at −15° to 25° C., with bromine in glacial acetic acid or aqueous acetic acid, with N-bromosuccinimide in ethanol, with tert.-butyl hypochdloride in methanol at −80° to −30° C., with iodobenzodichloride in aqueous pyridine at 0° to 50° C., with nitric acid in glacial acetic acid at 0° to 20° C., with chromic acid in glacial acetic acid or in acetone at 0° to 20° C. and with sulphuryl chloride in methylene chloride at −70° C., the thioether-chlorine complex hereby obtained preferably being hydrolysed with aqueous ethanol.

For the preparation of an alkylsulphonyl or alkylsulphonylmethyl compound of general formula (I), the oxidation is preferably carried out with one or with two or more equivalents of the oxidation agent employed, for example hydrogen peroxide in glacial acetic acid, trifluoroacetic acid or formic acid at 20° to 100° C. or in acetone at 0° to 60° C., with a per acid, such as performic acid or m-chloroperbenzoic acid in glacial acetic acid, trifluoroacetic acid, methylene chloride or chloroform at a temperature of from 0° to 60° C., with nitric acid in glacial acetic acid at 0° to 20° C., with chromic acid or potassium permanganate in glacial acetic acid, water/sulphuric acid or acetone at 0° to 20° C.

The preparation of compounds of general formula (I), in which $R_3$ is an alkanesulphonyloxy, trifluoromethanesulphonyloxy, alkanesulphonylamino, N-alkyl-alkanesulphonylamino, trifluoromethanesulphonylamino or N-alkyl-trifluoromethanesulphonylamino radical, is achieved by the subsequent reaction of a compound of the general formula:

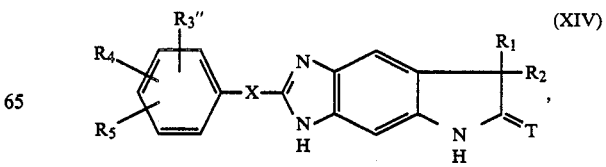

(XIV)

in which $R_1$, $R_2$, $R_4$, $R_5$, X and T have the above-given meanings and $R_3''$ is a hydroxyl or amino group or an N-alkylamino radical containing up to 3 carbon atoms in the alkyl moiety, with a sulphonic acid of the general formula:

$$R_8\text{—SO}_2\text{OH} \qquad \text{(XV)},$$

in which $R_8$ is an alkyl radical containing up to 3 carbon atoms or a trifluoromethyl radical, in the presence of an agent which removes water and/or activates the acid or the amine or with a functional derivative thereof.

The reaction is preferably carried out in a solvent or solvent mixture, such as methylene chloride, diethyl ether, tetrahydrofuran, dioxan or benzene, optionally in the presence of an acid-binding agent, such as sodium carbonate, triethylamine or pyridine, whereby the latter two can also be used as solvent, in the presence of an agent activating the acid or removing water, such as thionyl chloride or phosphorus pentachloride, but preferably with a reactive derivative of a compound of general formula (XV), for example with an anhydride or halide, such as methanesulphonic acid chloride or ethanesulphonic acid chloride, preferably at a temperature of from 0° to 100° C., for example at a temperature of from ambient temperature to 50° C.

The preparation of compounds of general formula (I), in which $R_2$ and/or $R_3$ is a carbonyl or sulphonyl group substituted by an amino, alkylamino, dialkylamino or hydrazino group, is achieved by the subsequent reaction of a compound of the general formula:

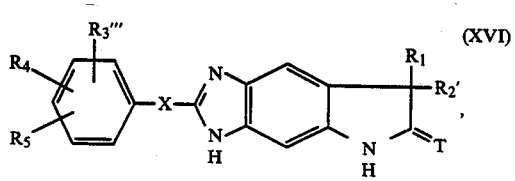

in which $R_1$, $R_4$, $R_5$, X and T have the above-given meanings and $R_2'$ and/or $R_3'''$ is a carboxyl or hydroxysulphonyl group, or a reactive derivative thereof, for example an ester or acid chloride, with hydrazine or an amine of the general formula:

in which $R_9$ and $R_{10}$, which are the same or different, are hydrogen atoms or alkyl radicals containing up to 5 carbon atoms, or with a reactive derivative thereof if $R_2'$ and/or $R_3'''$ is a carboxyl or hydroxysulphonyl group.

The reaction is preferably carried out in a solvent or solvent mixture, such as methylene chloride, ethanol, chloroform, carbon tetrachloride, diethyl ether, tetrahydrofuran, dioxan, benzene, toluene, acetonitrile or dimethylformamide, optionally in the presence of an agent activating the acid or removing water, for example in the presence of ethyl chloroformate, thionyl chloride, phosphorus trichloride, phosphorus pentoxide, N',N-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, or of an agent activating the hydrazino or amino group, for example phosphorus trichloride, and possibly in the presence of an inorganic base, such as sodium carbonate, or of a tertiary organic base, such as triethylamine or pyridine, which can simultaneously serve as a solvent, at a temperature of from −25° to 250° C. but preferably at a temperature of from −10° C. to the boiling temperature of the solvent used. Furthermore, water formed during the reaction can be removed by azeotropic destillation, for example by heating with toluene on a water separator, or by the addition of a drying agent, such as anhydrous magnesium sulphate or a molecular sieve.

However, the reaction is carried out especially advantageously in an appropriate halide, for example the carboxylic acid or sulphonic acid chloride, and hydrazine or a corresponding amine, in which case these can simultaneously serve as solvent, at a temperature of from 0° to 50° C., The preparation of compounds of general formula (I), in which $R_2$ is a cyano group, can be prepared by a subsequent reaction of a compound of the general formula:

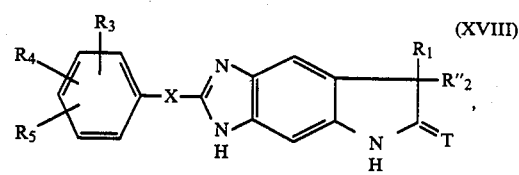

in which $R_1$, $R_3$, $R_4$, $R_5$, X and T have the above-given meanings and $R_2''$ is an aminocarbonyl group.

The reaction is preferably carried out in an inert solvent, for example methylene chloride, chloroform, dioxan, pyridine, xylene, chlorobenzene, in the presence of an agent removing water, for example, thionyl chloride, phosphorus trichloride, phosphoris pentoxide, phosphorus pentachloride, aluminium chloride, benzenesulphonic acid chloride, toluenesulphonic acid chloride, triphenyl phosphine, boron trifluoride or polyphosphoric acid ethyl ester, at a temperature of from 50° to 250° C. and preferably at the boiling temperature of the solvent employed.

If a compound is obtained of general formula (I), in which $R_2$ and/or $R_3$ is a cyano group, then this can subsequently be converted by alcoholysis and/or hydrolysis into a corresponding compound, in which $R_2$ and/or $R_3$ is an alkoxycarbonyl radical with a total of 2 to 5 carbon atoms, an aminocarbonyl or carboxyl group and/or $R_4$ is an alkoxycarbonyl radical with a total of 2 to 4 carbon atoms or the aminocarbonyl or carboxyl group and/or a compound of general formula (I), in which $R_2$ and/or $R_3$ is a carboxyl group, can be converted by esterification into a corresponding compound of general formula (I), in which $R_2$ and/or $R_3$ is an alkoxycarbonyl radical with a total of 2 to 5 carbon atoms.

The subsequent alcoholysis and/or hydrolysis is preferably carried out either in the presence of an acid, such as hydrochloric acid, sulphuric acid, phosphoric acid or trichloroacetic acid, or in the presence of a base, such as sodium hydroxide or potassium hydroxide, in an appropriate solvent, such as wter, water/methanol, ethanol, water/ethanol, water/isopropanol or water/dioxan, at a temperature of from −10° to 120° C., for example at a temperature of from ambient temperature to the boiling point of the reaction mixture.

The subsequent esterification is preferably carried out in an appropriate solvent, for example in a corresponding alcohol, pyridine, toluene, methylene chloride, tetrahydrofuran or dioxan, in the presence of an acid-activating agent and/or agent removing water, such as thionyl chloride, ethyl chloroformate, N,N'-carbonyldiimimidazole or N,N'-dicyclohexylcarbodiimide or the isothiourea ethers thereof, optionally in the presence of a reaction accel erator, such as copperr chloride, or is carried out by transesterification, for example with a corresponding carbonic acid ester, at a temperature of from 0° to 100° C. but preferably at a temperature of from 20° C. to the boiling point of the solvent used.

The preparation of compounds of general formula (I), in which T is a sulphur atom, can take place by subsequent conversion of a compound of general formula (I), in which T is an oxygen atom. THe reaction is carried out according to processes known from the literature with a reagent which transfers the sulphur atom, for example phosphorus pentasulphide, in which it is preferable to use 1 to 5 and more preferably 1 mole of phosphorus pentasulphide in an appropriate solvent. As solvent, there can be used, for example, tetrahydrofuran, dioxan, benzene, toluene or pyridine, at a temperature of from 25° to 125° C. However, it is preferred to use pyridine, the period of reaction being from 1 to 10 and preferably 5 hours, depending upon the reaction components.

Furthermore, the compounds obtained of general formula (I) can, if desired, subsequently be converted into their physiologically acceptable acid-addition salts with inorganic or organic acids. As acids to be used for this purpose, there may be mentioned, by way of example, hydrochloric acid, hydrobromic acid, sulphuric acid, phosphoric acid, fumaric acid, succinic acid, tartaric acid, citric acid, lactic acid, maleic acid and methanesulphonic acid.

The compounds of general formulae (II) to (V), (VIII) and (IX) used as starting materials are either known from the literature or can be prepared by processes known from the literature.

As already mentioned hereinbefore, the new compounds of general formula (I), the 1H tautomers thereof and the physiologically acceptable acid-addition salts thereof display, in the case of a long period of action, superior pharmacologically properties and especially a blood pressure-lowering and/or positive inotropic action and/or they influence the thrombocyte function and improve the microcirculation.

For the preparation of pharmaceutical compositions, the compounds according to the present invention are mixed in known manner with appropriate pharmaceutical carrier substances, aroma, flavouring and colouring materials and formed, for example, into tablets or dragees or, with the addition of apporopriate adjuvants, suspended or dissolved in water or an oil, for example olive oil.

The new compounds according to the present invention of general formula (I) and the salts thereof can be administered enterally or parenterally in liquid or solid form. As injection medium, it is preferred to use water which contains the additives usual in the case of injection solutions, such as stabilising agents, solubilising agents or buffers.

Additives of this kind include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The compounds according to the presen invention are usually administered in amounts of from 10 to 500 mg. per day, referred to a body weight of 75 kg. It is preferred to administer 1 to 2 tablets with an active material content of 5 to 200 mg. two or three times a day. The tablets can also be retarded, in which case it is only necessary to give 1 or 2 tablets with 10 to 500 mg. of active material once per day. The active material can also be administered by injection 1 to 8 times per day or by continuous infusion, in which case amounts of from 5 to mg./day normally suffice.

Apart from the compounds described in the following Examples, preferred compounds according to the present invention include the following, as well as the tautomers thereof:

7,7-dimethyl-2-(4-nitrophenyl)-6,7-dihydro-3H,5H-pyrrolo[2,3-f]benzimidazol-6-one 7,7-dimethyl-2-(4-aminophenyl)-6,7-dihydro-3H,5H-pyrrolo[2,3-f]benzimidazol-6-one 7,7-dimethyl-2-(2-hydroxyphenyl)-6,7-dihydro-3H,5H-pyrrolo[2,3-f]benzimidazol-6-one 7,7-dimethyl-(2-2-dimethylamino-4-nitrophenyl)-6,7-dihydro-3H,5H-pyrrolo[2,3-f]benzimidazol-6-one 7,7-dimethyl-2-(3,4-dichlorophenyl)-6,7-dihydro-3H,5H-pyrrolo[2,3-f]benzimidazol-6-one 7,7-dimethyl-2-(phenylvinyl)-6,7-dihydro-3H,5H-pyrrolo-[2,3-f]benzimidazol-6-one, mp. 320°–325° C.

7,7-dimethyl-2-(3,4-dimethoxyphenylvinyyl)-6,7-dihydro-3H,5H-pyrrolo[2,3-f]benzimidazol-6-one 7,7-dimethyl-2-(2-methoxy-4-aminocarbonylaminophenyl)-6,7-dihydro-3H,5H-pyrrolo[2,3-f]benzimidazol-6-one 7,7-dimethyl-2-(2-methoxy-4-methylaminocarbonylaminophenyl)-6,7-dihydro-3H,5H-pyrrolo[2,3-f]benzimidazol-6-one 7,7-dimethyl-2-(2-methoxy-4-trifluoromethylsulphonyloxyphenyl)-6,7-dihydro-3H,5H-pyrrolo[2,3-f]benzimidazol-6-one 7,7-dimethyl-2-(2-methoxy-4-ethylsulphonyloxyphenyl)-6,7-dihydro-3H,5H-pyrrolo[2,3-f]benzimidazol-6-one 7,7-dimethyl-2-(2-methoxy-4-aminosulphonylphenyl)-6,7-dihydro-3H,5H-pyrrolo[2,3-f]benzimidazol-6-one 7,7-dimethyl-2-(2-methoxy-4-dimethylaminosulphonylphenyl)-6,7-dihydro-3H,5H-pyrrolo[2,3-f]benzimidazol-6-one 7,7-dimethyl-2-(2-methoxy-4-n-butylaminosulphonylphenyl)-6,7-dihydro-3H,5H-pyrrolo[2,3-f]benzimidazol-6-one 7,7-dimethyl-2-[2-methoxy-4-(4-morpholinylsulphonyl)-phenyl]-6,7-dihydro-3H,5H-pyrrolo[2,3-f]benzimidazol-6-one 7,7-dimethyl-2-(2-methoxy-4-methylsulphenylmethylphenyl)-6,7-dihydro-3H,5H-pyrrolo[2,3-f]benzimidazol-6-one 7,7-dimethyl-2-(2-methoxy-4-methylsulphinylmethylphenyl)-6,7-dihydro-3H,5H-pyrrolo[2,3-f]benzimidazol-6-one 7,7-dimethyl-2-(2-methoxy-4-nitrophenyl)-6,7-dihydro-3H,5H-pyrrolo[2,3-f]benzimidazol-6-one 7,7-dimethyl-2-(2-methoxy-4-N-methylsulphonylaminophenyl)-6,7-dihydro-3H,5H-pyrrolo[2,3-f]benzimidazol-6-one 7,7-dimethyl-2-(2-methoxy-4-methylsulphinylphenyl)-6,7-dihydro-3H,5H-pyrrolo[2,3-f]benzimidazol-6-one, mp. 217°–220° C.

7,7-dimethyl-2-(4-trifluoromethylphenyl)-6,7-dihydro-3H,5H-pyrrolo[2,3-f]benzimidazol-6-one, mp. >300° C.

7,7-dimethyl-2-(2-methoxy-4-methylsulphonylmethylphenyl)-6,7-dihydro-3H,5H-pyrrolo[2,3-f]benzimidazol-6-one 7,7-dimethyl-2-(2-methoxy-4-methylaminosulphonylphenyl)-6,7-dihydro-3H,5H-pyrrolo[2,3-f]benzimidazol-6-one 7,7-dimethyl-2-(2-methoxy-4-propargyloxyphenyl)-6,7-dihydro-3H,5H-pyrrolo[2,3-f]benzimidazol-6-one 7,7-dimethyl-2-(2-methoxy-4-cyanomethoxyphenyl)-6,7-dihydro-3H,5H-pyrrolo[2,3-f]-benzimidazol-6-one 7,7-dimethyl-2-(2-methoxy-4-methoxycarbonylmethoxyphenyl)-6,7-dihydro-3H,5H-pyrrolo[2,3-f]benzimidazol-6-one 7,7-dimethyl-2-(3,4,5-trimethoxyphenyl)-6,7-dihydro-3H,5H-pyrrolo[2,3-f]benzimidazol-6-one 7,7-diethyl-2-phenyl-6,7-dihydro-3H,5H-pyrrolo[2,3-f]benzimidazol-6-one 7,7-diethyl-2-[4-(1H-imidazol-1-yl)-phenyl]-6,7-dihydro-3H,5H-pyrrolo[2,3-f]benzimidazol-6-one 7,7-diethyl-2-(2,4-dimethoxyphenyl)-6,7-dihydro-3H,5H-pyrrolo[2,3-f]benzimidazol-6-one 7,7-diethyl-2-(2-methoxy-4-hydroxyphenyl)-6,7-dihydro-3H,5H-pyrrolo[2,3-f]benzimidazol-6-one 7,7-diethyl-2-(2-methoxy-4-methylsulphonyloxyphenyl)-6,7-dihydro-3H,5H-pyrrolo[2,3-f]benzimidazol-6-one 7,7-diethyl-2-(2-methoxy-4-trifluoromethylsulphonyloxyphenyl)-6,7-dihydro-3H,5H-pyrrolo[2,3-f]benzimidazol-6-one 7,7-diethyl-2-(2-methoxy-4-methylsulphonylaminophenyl)-6,7-dihydro-3H,5H-pyrrolo[2,3-f]benzimidazol-6-one 7,7-diethyl-2-(2-methoxy-4-methylsulphenylmethylphenyl)-6,7-dihydro-3H,5H-pyrrolo[2,3-f]benzimidazol-6-one 7,7-diethyl-2-(2-methoxy-4-cyanophenyl)-6,7-dihydro-3H,5H-pyrrolo[2,3-f]benzimidazol-6-one 2'-phenyl-spiro[cyclopentan-1,7'-6',7'-dihydro-3'H,5'H-pyrrolo[2',3'-f]benzimidazol]-6'-one 2'-(2-methoxy-4-methylsulphonylaminophenyl)-spiro[cyclopentan-1,7'-6',7'-dihydro-3'H,5'H-pyrrolo[2',3'-f]-benzimidazol]-6'-one 2'-(2-methoxy-4-trifluoromethylsulphonyloxyphenyl)-spiro-[cyclopentan-1,7'-6',7'-dihydro-3'H,5'H-pyrrolo[2',3'-f]-benzimidazol]-6'-one 2'-(2-methoxy-4-nitrophenyl)-spiro[cyclopentan-1,7'-6',7'-dihydro-3'H,5'H-pyrrolo[2',3'-f]benzimidazol]-6'-one 2'-(2-methoxy-4-hydroxyphenyl)-spiro[cyclopentan-1,7'-6',7'-dihydro-3'H,5'H-pyrrolo[2',3'-f]benzimidazol]-6'-one 2'-(2-methoxy-4-aminophenyl)-spiro[cyclopentan-1,7'-6',7'-dihydro-3'H,5'H-pyrrolo[2',3'-f]benzimidazol]-6'-one 2'-(2-methoxy-4-methylsulphonyloxyphenyl)-spiro[cyclopentan-1,7'-6',7'-dihydro-3'H,5'H-pyrrolo[2',3'-f]-benzimidazol]-6'-one 7-methyl-2-phenyl-6,7-dihydro-3H,5H-pyrrolo[2,3-f]-benzimidazol-6-one 7-methyl-2-[4-(1H-imidazol-1-yl)-phenyl]-6,7-dihydro-3H,5H-pyrrolo[2,3-f]benzimidazol-6-one 7-methyl-2-(2-methoxy-4-methylsulphonylaminophenyl)-6,7-dihydro-3H,5H-pyrrolo[2,3-f]benzimidazol-6-one 7-methyl-2-(2-methoxy-4-ethylsulphonyloxyphenyl)-6,7-dihydro-3H,5H-pyrrolo[2,3-f]benzimidazol-6-one 7-methyl-2-(2-methoxy-4-trifluoromethylsulphonyloxyphenyl)-6,7-dihydro-3H,5H-pyrrolo[2,3-f]benzimidazol-6-one 7-methyl-2-(4-dimethylaminophenyl)-6,7-dihydro-3H,5H-pyrrolo[2,3-f]benzimidazol-6-one 7-methyl-2-(2-dimethylamino-4-nitrophenyl)-6,7-dihydro-3H,5H-pyrrolo[2,3-f]benzimidazol-6-one 7-methyl-2-(2-methoxy-4-nitrophenyl)-6,7-dihydro-3H,5H-pyrrolo[2,3-f]benzimidazol-6-one 7-methyl-2-(2-methoxy-4-hydroxyphenyl)-6,7-dihydro-3H,5H-pyrrolo[2,3-f]benzimidazol-6-one 7-methyl-2-(2-methoxy-4-aminocarbonylaminophenyl)-6,7-dihydro-3H,5H-pyrrolo[2,3-f]benzimidazol-6-one 7-methyl-2-(2-methoxy-4-cyanophenyl)-6,7-dihydro-3H,5H-pyrrolo[2,3-f]benzimidazol-6-one 7-methyl-2-(2-methoxy-4-methylsulphonyloxyphenyl)-6,7-dihydro-3H,5H-pyrrolo[2,3-f]benzimidazol-6-one 7-methyl-2-(2-methoxy-4-methylsulphinylmethylphenyl)-6,7-dihydro-3H,5H-pyrrolo[2,3-f]benzimidazol-6-one 7-methyl-2-(2-methoxy-4-aminosulphonylphenyl)-6,7-dihydro-3H,5H-pyrrolo[2,3-f]benzimidazol-6-one 7-methyl-2-(2-methoxy-4-methylaminosulphonylphenyl)-6,7-dihydro-3H,5H-pyrrolo[2,3-f]benzimidazol-6-one 7-ethyl-2-phenyl-6,7-dihydro-3H,5H-pyrrolo[2,3-f]-benzimidazol-6-one 7-ethyl-2-[4-(1H-imidazol-1-yl)-phenyl]-6,7-dihydro-3H,5H-pyrrolo[2,3-f]benzimidazol-6-one 7-ethyl-2-(2-methoxy-4-methylsulphonylaminophenyl)-6,7-dihydro-3H,5H-pyrrolo[2,3-f]benzimidazol-6-one 7-ethyl-2-(2-methoxy-4-N-methyl-methylsulphonylaminophenyl)-6,7-dihydro-3H,5H-pyrrolo[2,3-f]benzimidazol-6-one 7-ethyl-2-(2-methoxy-4-methylsulphonylmethylphenyl)-6,7-dihydro-3H,5H-pyrrolo[2,3-f]benzimidazol-6-one 7-ethyl-2-(2-methoxy-4-ethylsulphonyloxyphenyl)-6,7-dihydro-3H,5H-pyrrolo[2,3-f]benzimidazol-6-one 7-ethyl-2-(3-methoxy-4-methylsulphonylaminophenyl)-6,7-dihydro-3H,5H-pyrrolo[2,3-f]benzimidazol-6-one 7-ethyl-2-(2-methoxy-4-trifluoromethylsulphonyloxyphenyl)-6,7-dihydro-3H,5H-pyrrolo[2,3-f]benzimidazol-6-one 7-ethyl-2-(2-methoxy-4-nitrophenyl)-6,7-dihydro-3H,5H-pyrrolo[2,3-f]benzimidazol-6-one 7-ethyl-2-(3,4-dimethoxyphenylvinyl)-6,7-dihydro-3H,5H-pyrrolo[2,3-f]benzimidazol-6-one 7-ethyl-2-(2-methoxy-4-hysroxyphenyl)-6,7-dihydro-3H,5H-pyrrolo[2,3-f]benzimidazol-6-one 7-ethyl-2-(3,4-dichlorophenyl)-6,7-dihydro-3H,5H-pyrrolo[2,3-f]benzimidazol-6-one 7-ethyl-2-(2-methoxy-4-methylaminocarbonylaminophenyl)-6,7-dihydro-3H,5H-pyrrolo[2,3-f]benzimidazol-6-one 7-ethyl-2-(2-methoxy-4-methylsulphonyloxyphenyl)-6,7-dihydro-3H,5H-pyrrolo[2,3-f]benzimidazol-6-one 7-isopropyl-2-phenyl-6,7-dihydro-3H,5H-pyrrolo[2,3-f]-benzimidazol-6-one 7-isopropyl-2-[4-(1H-imidazol-1-yl)-phenyl]-6,7-dihydro-3H,5H-pyrrolo[2,3-f]benzimidazol-6-one 7-isopropyl-2-(2-methoxy-4-methylsulphonyloxyphenyl)-6,7-dihydro-3H,5H-pyrrolo[2,3-f]benzimidazol-6-one 7-isopropyl-2-(2-methoxy-4-methylaminocarbonylaminophenyl)-6,7-dihydro-3H,5H-pyrrolo[2,3-f]benzimidazol-6-one 7-isopropyl-2-(2-methoxy-4-methylsulphonylaminophenyl)-6,7-dihydro-3H,5H-pyrrolo[2,3-f]benzimidazol-6-one 7-isopropyl-2-(2-methoxy-4-nitrophenyl)-6,7-dihydro-3H,5H-pyrrolo[2,3-f]benzimidazol-6-one 7-isopropyl-2-(2-methoxy-4-aminophenyl)-6,7-dihydro-3H,5H-pyrrolo[2,3-f]benzimidazol-6-one 7-isopropyl-2-(2-methoxy-4-hydroxyphenyl)-6,7-dihydro-3H,5H-pyrrolo[2,3-f]benzimidazol-6-one 7-isopropylidene-2-(2-methoxy-4-hydroxyphenyl)-6,7-dihydro-3H,5H-pyrrolo[2,3-f]benzimidazol-6-one 7-acetyl-2-(4-methoxyphenyl)-6,7-dihydro-3H,5H-pyrrolo-[2,3-f]benzimidazol-6-one 7-acetyl-2-(2-methoxy-4-methylsulphonyloxyphenyl)-6,7-dihydro-3H,5H-pyrrolo[2,3-f]benzimidazol-6-one 7-acetyl-2-(2-methoxy-4-methylsulphonylaminophenyl)-6,7-dihydro-3H,5H-pyrrolo[2,3-f]benzimidazol-6-one 7-acetyl-7-methyl-2-(4-methoxyphenyl)-6,7-dihydro-3H,5H-pyrrolo[2,3-f]benzimidazol-6-one 7-acetyl-7-methyl-2-(2-methoxy-4-hydroxyphenyl)-6,7-dihydro-3H,5H-pyrrolo[2,3-f]benzimidazol-6-one 7-acetyl-7-methyl-2-(2-methoxy-4-methylsulphonylaminophenyl)-6,7-dihydro-3H,5H-pyrrolo[2,3-f]benzimidazol-6-one 7-acetyl-7-methyl-2-(2-methoxy-4-methylsulphonyloxyphenyl)-6,7-dihydro-3H,5H-pyrrolo[2,3-f]benzimidazol-6-one 7-methoxycarbonyl-2-(4-methoxyphenyl)-6,7-dihydro-3H,5H-pyrrolo[2,3-f]benzimidazol-6-one 7-methoxycarbonyl-2-(2-methoxy-4-methylsulphonyloxyphenyl)-6,7-dihydro-3H,5H-pyrrolo[2,3-f]benzimidazol-6-one 7-methoxycarbonyl-2-(2-methoxy-4-methylsulphonylaminophenyl)-6,7-dihydro-3H,5H-pyrrolo[2,3-f]benzimidazol-6-one 7-ethoxycarbonyl-7-ethyl-2-(4-methoxyphenyl)-6,7-dihydro-3H,5H-pyrrolo[2,3-f]benzimidazol-6-one 7-ethoxycarbonyl-7-ethyl-2-(2-methoxy-4-methylsulphonyloxyphenyl)-6,7-dihydro-3H,5H-pyrrolo[2,3-f]benzimidazol-6-one 7-ethoxycarbonyl-7-ethyl-2-(2-methoxy-4-methylsulphonylaminophenyl)-6,7-dihydro-3H,5H-pyrrolo[2,3-f]benzimidazol-6-one 7-ethoxycarbonyl-7-methyl-2-[4-(1H-imidazol-1-yl)-phenyl]-6,7-dihydro-3H,5H-pyrrolo[2,3-f]benzimidazol-6-one 7-ethoxycarbonyl-7-methyl-2-(2-methoxy-4-hydroxyphenyl)-6,7-dihydro-3H,5H-pyrrolo[2,3-f]benzimidazol-6-one 7-ethoxycarbonyl-7-methyl-2-(2-methoxy-4-methylsulphonylaminophenyl)-6,7-dihydro-3H,5H-pyrrolo[2,3-f]benzimidazol-6-one 7-ethoxycarbonyl-7-methyl-2-(2-methoxy-4-methylsulphonyloxyphenyl)-6,7-dihydro-3H,5H-pyrrolo[2,3-f]benzimidazol-6-one 7-aminocarbonyl-7-methyl-2-(4-methoxyphenyl)-6,7-dihydro-3H,5H-pyrrolo[2,3-f]benzimidazol-6-one 7-aminocarbonyl-7-methyl-2-(2-methoxy-4-methylsulphonyloxyphenyl)-6,7-dihydro-3H,5H-pyrrolo[2,3-f]benzimidazol-6-one 7-aminocarbonyl-7-methyl-2-(2-methoxy-4-methylsulphonylaminophenyl)-6,7-dihydro-3H,5H-pyrrolo[2,3-f]benzimidazol-6-one 7-cyano-7-methyl-2-(4-methoxyphenyl)-6,7-dihydro-3H,5H-pyrrolo[2,3-f]benzimidazol-6-one 7-cyano-7-methyl-2-(2-methoxy-4-methylsulphonyloxyphenyl)-6,7-dihydro-3H,5H-pyrrolo[2,3-f]benzimidazol-6-one 7-cyano-7-methyl-2-(2-methoxy-4-methylsulphonylaminophenyl)-6,7-dihydro-3H,5H-pyrrolo[2,3-f]benzimidazol-6-one 7-hydrazinocarbonyl-7-methyl-2-(4-methoxyphenyl)-6,7-dihydro-3H,5H-pyrrolo[2,3-f]benzimidazol-6-one The following Examples are given for the purpose of illustrating the present invention:

EXAMPLE 1

7-Isopropyl-2-(4-methoxyphenyl)-6,7-dihydro-3H,5H-pyrrolo[2,3-f]benzimidazol-6-one 2.8 g. (13.6 mmol) 5,6-diamino-3-isopropylindolin-2-one dihydrochloride were suspended in 10 ml. methylene chloride, mixed with 2.55 g. (15 mmol) p-methoxybenzoyl chloride and 4.55 g. (45 mmol) triethylamine added dropwise thereto at 25° C. The reaction mixture was stirred for 2 hours, evaporated and worked up with water. The residue was heated under reflux for about 24 hours in 75 ml. ethanol and 75 ml. concentrated hydrochloric acid, evaporated and rendered neutral with 2N ammonia solution. The residue filtered off with suction was recrystallised from ethyl acetate/methanol. There were obtained 2.1 g. (48.2% of theory) of the title compound; m.p. 326°-328° C.

The following compounds were obtained in a manner analogous to that described in Example 1:

| | designation | yield % | m.p. in °C. (solvent) |
|---|---|---|---|
| 1A | 7,7-dimethyl-2-phenylmethyl-6,7-dihydro-3H,5H—pyrrolo-[2,3-f]benzimidazol-6-one from 5,6-diamino-3,3-dimethyl-indolin-2-one and phenyl-acetyl chloride | 45 | 328-330 ethanol/water |
| 1B | 7,7-dimethyl-2-(2-methoxy-phenyl)-6,7-dihydro-3H,5H—pyrrolo[2,3-f]benzimidazol-6-one from 5,6-diamino-3,3-dimethyl-indolin-2-one and 2-methoxy-benzoyl chloride | 23 | 300-303 acetone |
| 1C | 7,7-dimethyl-2-(4-methoxy-phenyl)-6,7-dihydro-3H,5H—pyrrolo[2,3-f]benzimidazol-6-one from 5,6-diamino-3,3-dimethyl-indolin-2-one and 4-methoxy-benzoyl chloride | 46 | 341-343 dioxan/water 2:1 |
| 1D | 7,7-dimethyl-2-(4-chloro-phenyl)-6,7-dihydro-3H,5H—pyrrolo[2,3-f]benzimidazol-6-one from 5,6-diamino-3,3-dimethyl-indolin-2-one and 4-chloro-benzoyl chloride | 11 | 360-363 acetone |
| 1E | 7,7-dimethyl-2-(2-methoxy-5-methyl-sulphonylphenyl)-6,7-dihydro-3H,5H—pyrrolo[2,3-f]benzimidazol-6-one | 29 | 236-238 ethanol/water |

-continued

| designation | yield % | m.p. in °C. (solvent) |
|---|---|---|
| from 5,6-diamino-3,3-dimethylindolin-2-one and 2-methoxy-5-methyl-sulphonylbenzoyl chloride | | |
| 1F 7,7-dimethyl-2-(4-methylphenyl)-6,7-dihydro-3H,5H—pyrrolo-[2,3-f]benzimidazol-6-one from 5,6-diamino-3,3-dimethylindolin-2-one and 4-methylbenzoyl chloride | 30 | >300 isopropanol |
| 1G 7,7-diethyl-2-(4-methoxyphenyl)-6,7-dihydro-3H,5H—pyrrolo-[2,3-f]-benzimidazol-6-one from 5,6-diamino-3,3-diethylindolin-2-one and 4-methoxybenzoyl chloride | 44 | 217–219 ethyl acetate |
| 1H 2'-(4-methoxyphenyl)-spiro[cyclopentane-1,7'-6',7'-dihydro-3'H,5'H—pyrrolo[2',3'-f]benzimidazol]-6'-one from 5',6'-diamino-spiro[cyclopentane-1,3'-indolin]-2'-one and 4-methoxybenzoyl chloride | 37 | 354–355 dioxan/water 1:1 |
| 1I 7-methyl-2-(4-methoxyphenyl)-6,7-dihydro-3H,5H—pyrrolo[2,3-f]-benzimidazol-6-one from 5,6-diamino-3-methylindolin-2-one and 4-methoxybenzoyl chloride | 43 | >300 ethyl acetate/methanol |
| 1J 7-methyl-2-(4-dimethoxyphenyl)-6,7-dihydro-3H,5H—pyrrolo[2,3-f]-benzimidazol-6-one from 5,6-diamino-3-methylindolin-2-one and 2,4-dimethoxybenzoyl chloride | 12 | 294–297 ethyl acetate/methanol |

EXAMPLE 2

7,7-Dimethyl-2-(4-hydroxyphenyl)-6,7-dihydro-3H,5H-pyrrolo[2,3-f]benzimidazol-6-one A solution of 3.6 g. (0.019 mol) 5,6-diamino-3,3-dimethyloxindole and 4.0 g. (0.019 mol) 4-benzyloxy-benzaldehyde in 100 ml. ethanol was heated to the boil while passing through air. After 1 hour, the reaction mixture was cooled and the precipitate obtained was filtered off with suction. There were obtained 5.4 g. (74% of theory) of colourless crystals; m.p. 250° C.

5.4 g. (0.014 mol) of this compound were hydrogenated in 200 ml. methanol in the presence of 0.5 g. 10% palladium/charcoal at normal pressure. Thereafter, the catalyst was filtered off with suction and the solvent evaporated off from the filtrate in a vacuum. There were obtained 1.8 g. (44% of theory) of the title compound in the form of colourless crystals; m.p. 240° C. (recrystallised from acetone).

EXAMPLE 3

7,7-Dimethyl-2-phenyl-6,7-dihydro-3H,5H-pyrrolo[2,3-f]benzimidazol-6-one (a) 5.6 ml. (50 mmol) benzoyl chloride were added dropwise to a solution of 5.5 g. (25 mmol) 6-amino-5-nitro-3,3-dimethylindolin-2-one in 50 ml. pyridine, while cooling with ice, followed by stirring at 25° C. The crystalline slurry obtained was poured on to about 300 ml. water, filtered off with suction and washed with water and dried. There were obtained 10.7 g. 6-benzoylamino-5-nitro-3,3-dimethylindolin-2-one.

(b) 1.0 g. palladium/charcoal (10%) were introduced into 10.0 g. (30.7 mmol) 6-benzoylamino-5-nitro-3,3-dimethylindolin-2-one in 250 ml. glacial acetic acid. This mixture was hydrogenated in a shaking bomb at ambient temperature and normal pressure. After the take up of hydrogen had ceased, the solution was separated from the catalyst, slowly evaporated at 60° C. and the residue taken up in water and neutralised with 2N aqueous ammonia solution. The precipitate was filtered off with suction and recrystallised from methylene chloride. There were obtained 6.9 g. (81% of theory) of the title compound; m.p. 195°–220° C.

The following compounds were obtained in a manner analogous to that described in Example 3:

| | designation | yield % | m.p. in °C. (solvent) |
|---|---|---|---|
| 3A | 7,7-dimethyl-2-(2,4-dimethoxyphenyl)-6,7-dihydro-3H,5H—pyrrolo[2,3-f]benzimidazol-6-one from 5-(2,4-dimethoxybenzoylamino)-6-nitro-3,3-dimethyl-indolin-2-one | 25 | 294–297 dioxan |
| 3B | 7,7-dimethyl-2-(3,4-dimethoxyphenyl)-6,7-dihydro-3H,5H—pyrrolo[2,3-f]benzimidazol-6-one from 6-(3,4-dimethoxybenzoylamino)-5-nitro-3,3-dimethylindolin-2-one | 75 | 314–317 ethanol |
| 3C | 7,7-dimethyl-2-(2-methoxy-4-chlorophenyl)-6,7-dihydro-3H,5H—pyrrolo[2,3-f]benzimidazol-6-one from 6-(2-methoxy-4-chlorobenzoylamino)-5-nitro-3,3-dimethyl-indolin-2-one | 12 | 299–301 ethanol |

EXAMPLE 4

7-Methyl-2-(2-methoxy-4-aminophenyl)-6,7-dihydro-3H,5H-pyrrolo[2,3-f]benzimidazol-6-one hydrochloride (a) 3.5 g. (14 mmol) 5,6-diamino-3-methylindolin-2-one dihydrochloride, 4.5 g. (21 mmol) 2-methoxy-4-nitro-benzoyl chloride and 6.95 g. (49 mmol) triethylamine were stirred at ambient temperature for 3 hours in 50 ml. methylene chloride. Subsequently, the reaction mixture was distilled to dryness and the residue was worked up with water and recrystallised from methanol/methylene chloride. There was obtained a mixture of mono- and diamide.

(b) 2.6 g. of the product so obtained were hydrogenated in 400 ml. methanol in the presence of 0.8 g. palladium/charcoal. When the take up of hydrogen had ceased, the catalyst was filtered off with suction, the methanol was distilled off and the residue was boiled with 70 ml. ethanol and 35 ml. concentrated hydrochloric acid for 24 hours. The solvent was distilled off and the oily residue was crystallised from ethanol. There was obtained 1.1 g. of the title compound; m.p. 280°–310° C.

The following compounds were obtained in a manner analogous to that described in Example 4:

| | designation | yield % | m.p. in °C. (solvent) |
|---|---|---|---|
| 4A | 7,7-dimethyl-2-(2-methoxy-4-aminophenyl)-6,7-dihydro-3H,5H—pyrrolo[2,3-f]benzimidazol-6-one hydrochloride | 18 | 295 ethanol |
| 4B | 7-ethyl-2-(2-methoxy-4-aminophenyl)-6,7-dihydro-3H,5H—pyrrolo[2,3-f]benzimidazol- | 10 | 274 ethanol |

-continued

| designation | yield % | m.p. in °C. (solvent) |
| --- | --- | --- |
| 6-one hydrochloride | | |

EXAMPLE 5

7-Ethyl-2-(2-methoxy-4-acetylaminophenyl)-6,7-dihydro-3H,5H-pyrrolo[2,3-f]benzimidazol-6-one 0.7 g. (1.8 mmol) 7-ethyl-2-(2-methoxy-4-aminophenyl)-6,7-dihydro-3H,5H-pyrrolo[2,3-f]benzimiazol-6-one hydrochloride, 15 ml. acetic anhydride and 0.3 g. sodium acetate were stirred for 3 hours at 40° C. After cooling, the product was filtered off with suction and, after treatment with charcoal, crystallised from methanol. There was obtained 0.44 g. (69% of theory) of the title compound; m.p. 245°–249° C.

EXAMPLE 6A 7,7-Dimethyl-2-[4-(1H-imidazol-1-yl)-phenyl]-6,7-dihydro-3H,5H-pyrrolo[2,3-f]benzimidazol-6-one 2.0 g. (10.4 mmol) 5,6-diamino-3,3-dimethyl-indolin-2-one, 1.8 g. (10.4 mmol) 4-(1H-imidazol-1-yl)-benzaldehyde, 0.2 g. (1 mmol) p-toluenesulphonic acid and 120 ml. ethanol were mixed together, heated to the boiling point and air passed therethrough for 3 hours. After concentration and acidification with ethanolic hydrochloric acid, the crystallisate obtained was filtered off with suction, suspended in water and neutralised with an aqueous solution of ammonia. The residue obtained was recrystallised from methanol. There was obtained 1.0 g. (28% of theory) of the title compound; m.p. 300° C.

EXAMPLE 6B

In a manner analogous to that described in Example 6, from 5,6-diamino-3,3-dimethylindolin-2-one and 4-dimethyliaminobenzaldehyde, there was obtained, in a yield of 23% of theory, 7,7-dimethyl-2-(4-dimethylaminophenyl)-6,7-dihydro-3H,5H-pyrrolo[2,3-f]benzimidazol-6-one hydrochloride; m.p. 262°–270° C. (after recrystallisation from isopropanol).

EXAMPLE 7

7,7-Dimethyl-2-(2-methoxy-4-methylthiophenyl)-6,7-dihydro-3H,5H-pyrrolo[2,3-f]benzimidazol-6-one 7.65 g. (50 mmol) phosphorus oxychloride were added dropwise at 25° C. to a solution of 5.5 g. (25 mmol) 6-amino-5-nitro-3,3-dimethylindolin-2-one and 9.9 g. (50 mmol) 2-methoxy-4-methylthiobenzoic acid in 50 ml. pyridine. Working up and subsequent hydrogenation took place in a manner analogous to that described in Example 3. There were obtained 5.3 g. (60% of theory) of the title compound; m.p. 293°–295° C.

EXAMPLE 8

7,7-Dimethyl-2-(2-methoxy-4-methylsulphonylaminophenyl)-6,7-dihydro-3H,5H-pyrrolo[2,3-f]benzimidazol-6-one 1.26 g. (11 mmol) methanesulphonyl chloride were slowly added dropwise to a solution of 3.6 g. (10 mmol) 7,7-dimethyl-2-(2-methoxy-4-aminophenyl)-6,7-dihydro-3H,5H-pyrrolo[2,3-f]benzimidazol-6-one hydrochloride and 2.2 g. (22 mmol) triethylamine in 50 ml. dimethylformamide. After stirring for 2 hours at 25° C., the dimethylformamide was distilled off under a high vacuum. The residue was worked up with water and filtered off with suction. Subsequently, it was recrystallised from ethanol to give 2.9 g. (72.5% of theory) of the title compound; m.p. >300° C.

EXAMPLE 9

7,7-Dimethyl-2-(2-methoxy-4-cyanophenyl)-6,7-dihydro-3H,5H-pyrrolo[2,3-f]benzimidazol-6-one 22.9 g. (0.11 mol) phosphorus pentachloride were added portionwise, while cooling, to 17.7 g. 4-cyano-2-methoxybenzoic acid (0.1 mol; m.p. 170°–173° C.) in 180 ml. dichloromethane. The solvent was removed under a vacuum and the residue (acid chloride) further reacted without purification.

9.8 g. (0.05 mol) of this residue were taken up in 50 ml. dichloromethane, 6.9 g. (0.05 mol) triethylamine and 5.7 g. (0.03 mol) 5,6-diamino-3,3-dimethyloxindole were added thereto and the reaction mixture stirred at ambient temperature. After filtration, the solvent was removed in a vacuum and the residue further reacted without purification.

5.3 g. of the residue were heated under reflux for 3 hours in 200 ml. ethanol and 30 ml. concentrated hydrochloric acid. The solvent was removed in a vacuum, and the residue digested with an aqueous solution of ammonia. After chromatographic purification over silica gel using dichloromethane:methanolic ammonia solution (2:1 v/v) and toluene:ethyl acetate:acetic acid 5:5:1 v/v/v), there was obtained 1.4 g. of the title compound in the form of its acetate; m.p. 304°–312° C.

EXAMPLE 10

7,7-Dimethyl-2-(2-methoxy-4-carboxyphenyl)-6,7-dihydro-3H,5H-pyrrolo[2,3-f]benzimidazol-6-one 0.4 g. (1.2 mmol) 3,3-dimethyl-2-(2-methoxy-4-cyanophenyl)-6,7-dihydro-3H,5H-pyrrolo[2,3-f]benzimidazol-6-one was heated under reflux for 1 hour with 4 ml. 2N aqueous sodium hydroxide solution. Subsequently, the reaction mixture was cooled, acidified with glacial acetic acid and the crystallisate obtained was filtered off with suction. There was obtained 0.4 g. (95% of theory) of the title compound; m.p. 315°–319° C.

EXAMPLE 11

7,7-Dimethyl-2-(2-methoxy-4-aminocarbonylphenyl)-6,7-dihydro-3H,5H-pyrrolo[2,3-f]benzimidazol-6-one 0.25 g. (0.71 mmol) 7,7-dimethyl-2-(2-methoxy-4-carboxyphenyl)-6,7-dihydro-3H,5H-pyrrolo[2,3-f]benzimidazol-6-one were boiled under reflux for 3 hours with 2 ml. thionyl chloride. Subsequently, the reaction mixture was evaporated to dryness and the acid chloride obtained was suspended in 2 ml. dioxan and 2 ml. concentrated aqueous ammonia solution added dropwise thereto. Stirring was continued for 1 hour at 80° C., the dioxan and water were distilled off, the residue was stirred with water and then filtered off with suction. There was obtained 0.15 g. (60% of theory) of the title compound; m.p. 265°–270° C.

EXAMPLE 12

7,7-Dimethyl-2-(2-methoxy-4-ethoxycarbonylphenyl)-6,7-dihydro-3H,5H-pyrrolo[2,3-f]benzimidazol-6-one 0.25 g. (0.71 mmol) 7,7-dimethyl-2-(2-methoxy-4-carboxyphenyl)-6,7-dihydro-3H,5H-pyrrolo[2,3-f]benzimidazol-6-one was boiled under reflux for 3 hours with 2 ml. thionyl chloride and subsequently evaporated to dryness. The acid chloride obtained was mixed with 5 ml. ethanol and boiled under reflux for 1 hour, cooled and crystallisate formed was filtered off with suction. There was obtained 0.16 g. (59% of theory) of the title compound; m.p. 235°–240° C.

EXAMPLE 13

7,7-Dimethyl-2-(2-methoxy-4-hydroxyphenyl)-6,7-dihydro-3H,5H-pyrrolo[2,3-f]benzimidazol-6-one In a manner analogous to that described in Example 1, from 2.0 g. (10.4 mmol) 5,6-diamino-3,3-dimethylindolin-2-one and 5.75 g. (20.8 mmol) 4-benzyloxyo-2-methoxybenzoyl chloride, there was obtained 2.1 g. (62.5% of theory) of the title compound; m.p. 225°–240° C. (decomp.).

EXAMPLE 14

7,7-Dimethyl-2-(2-methoxy-4-methylsulphonyloxyphenyl)-6,7-dihydro-3H,5H-pyrrolo[2,3-f]benzimidazol-6-one 0.53 g. (4.6 mmol) methanesulphonyl chloride was added dropwise at 25° C. to a solution of 1.5 g. (4.6 mmol) 7,7-dimethyl-2-(2-methoxy-4-hydroxyphenyl)-6,7-dihydro-3H,5H-pyrrolo[2,3-f]benzimidazol-6-one and 0.46 g. (4.6 mmol) triethylamine in 20 ml. dimethylformamide. After 2 hours, the dimethylformamide was distilled off in a vacuum. The residue was worked up with water and filtered off with suction. The residue was recrystallised from ethanol. There were obtained 1.3 g. (70.6% of theory) of the title compound; m.p. 233°–235° C.

EXAMPLE 15

7-Ethoxycarbonyl-7-methyl-2-phenyl-6,7-dihydro-3H,5H-pyrrolo[2,3-f]benzimidazol-6-one (a) 4 g. (14.8 mmol) 3-ethoxycarbonyl-3-methyl-6-amino-indolin-2-one hydrochloride and 2.99 g. (29.6 mmol) triethylamine were suspended in 60 ml. methylene chloride and, while cooling with ice, 2.08 g. (14.8 mmol) benzoyl chloride were added dropwise thereto. After 2 hours, the methylene chloride was distilled off, the residue was worked up with water, filtered with suction and crystallised from ethanol. There were obtained 3.5 g. (70% of theory) 3-ethoxycarbonyl-3-methyl-6-benzoylaminoindolin-2-one; m.p. 206°–207° C.

(b) 3 g. (8.86 mmol) of the compound obtained according to (a) above were dissolved in 20 ml. concentrated sulphuric acid. 0.985 g. (9.75 mmol) potassium nitrate, dissolved in concentrated sulphuric acid, were slowly added dropwise thereto at 0° to 5° C. After 3 hours, the the reaction mixture was poured on to ice, filtered with suction, the residue suspended in water, neutralised with aqueuous ammonia solution, filtered off with suction and the product obtained was recrystallised from ethanol. There were obtained 2.75 g. (81% of theory) 3-ethoxycarbonyl-3-methyl-5-nitro6-benzoylaminoindolin-2-one; m.p. 220°–223° C.

(c) 0.5 g. palladium/charcoal (10%) was added to 2.55 g. (6.66 mmol) of the compound obtained according to (b) above in 100 ml. glacial acetic acid. This suspension was hydrogenated at ambient temperature and normal pressure. After ending of the take up of hydrogen, the solution was separated from the catalyst, slowly evaporated at 60° C. and the residue was taken up in water, neutralised with 2N aqueous ammonia solution and filtered with suction. After recrystallisation from ethanol, there was obtained 1.3 g. (62% of theory) of the title compound; m.p. 178°–182° C.

EXAMPLE 16

7,7-Dimethyl-2-(2-methoxy-4-methylsulphonylphenyl)-6,7-dihydro-3H,5H-pyrrolo[2,3-f]benzimidazol-6-one 200 mg. (0.56 mmol) 7,7-dimethyl-2-(2-methoxy-4-methylthiophenyl)-6,7-dihydro-3H,5H-pyrrolo[2,3-f]-benzimidazol-6-one were stirred for 48 hours at ambient temperature in 4 ml. glacial acetic acid and 0.4 ml. 30% hydrogen peroxide. 10 ml. water were added thereto and the solvent was removed in a vacuum. There were obtained 160 mg. (75% of theory) of the title compound which, after crystallization from ethanol, had a melting point of 235°–237° C.

EXAMPLE 17

Analogously to example 15a, 6-amino-3,3-dimethylindolin-2-one is reacted with the following acid chlorides to yield the following amides:

| Compound | Yield % | mp [°C.] recrystall. solvent |
| --- | --- | --- |
| (a) 3,3-Dimethyl-6-(3-phenyl-propenoylamino) indolin-2-one from cinnamoyl chloride | 60 | 272–75 CH₃OH/DMSO |
| (b) 3,3-Dimethyl-6-benzoylamino-indolin-2-one from benzoyl chloride | 50 | 250–54 CH₃OH |
| (c) 3,3-Dimethyl-6-(2-methoxy-benzoylamino)indolin-2-one from 2-methoxybenzoyl chloride | 72 | 190–92 CH₃OH |
| (d) 3,3-Dimethyl-6-(4-methoxy-benzoylamino)indolin-2-one from 4-methoxybenzoyl chloride | 64 | 253–55 EtOH |
| (e) 3,3-Dimethyl-6-(4-methyl-benzoylamino)indolin-2-one from 4-methylbenzoyl chloride | 55 | 274–78 EtOH/CH₃OH |
| (f) 3,3-Dimethyl-6-(4-trifluor-methylbenzoylamino)indolin-2-one from 4-trifluormethyl-benzoyl chloride | 67 | 244–46 EtOH |
| (g) 3,3-Dimethyl-6-(2-methoxy-4-methylsulfonylbenzoyl-amino)indolin-2-one from 2-methoxy-4-methyl-sulfonylbenzoyl chloride | 42 | 270–73 EtOH |

EXAMPLE 18

Analogously to example 15a, 6'-amino-spiro(cyclopentan-1,3'-indolin)-2'-one is reacted with the following acid chlorides to yield the following amides:

| Compound | Yield % | mp [°C.] recrystall. solvent |
| --- | --- | --- |
| (a) 6'-(4-Methoxybenzoylamino)-spiro(cyclopentan-1,3'-indolin)-2'-one from 4-methoxybenzoyl chloride | 66 | 251–53 CH₃OH |

EXAMPLE 19

Analogously to example 15a, 5-amino-3,3-dimethyl-indolin-2-one is reacted with the following acid chlorides to yield the following amides:

| Compound | Yield % | mp [°C.] recrystall. solvent |
|---|---|---|
| (a) 3,3-Dimethyl-5-benzoylamino-indolin-2-one from benzoyl chloride | 56 | 210–12 EtOH |
| (b) 3,3-Dimethyl-5-(2-methoxy-benzoylamino)indolin-2-one from 2-methoxybenzoyl chloride | 30 | 186–88 EtOH |

The following tests were run to show the pharmaceutical activity of the compounds described above. Testing was done along with reference compounds for comparison.

Examination Method

Male Sprague-Dawley rats weighing between 350 and 450 g were narcotized by intraperitoneal injection of a barbiturate and fitted with instrumentation for the examinations as follows:

A pressure measuring catheter (Millar Mikrotip/diameter 0.5 mm) was inserted through the arteria carotis dextra into the left ventricle. The pressure inside the left ventricle was continually registered through this catheter. The signal from this Mikrotip was electronically differentiated and $(dp/dt)_{60}$—the slope of the pressure-time curve at a pressure of 60 mmHg—was taken as a measure for the inotropy.

A polypropylene catheter was bound in a vena jugularis for the intravenous injection of the test substances.

A further polyproylene catheter was inserted through an arteria femoralis into the abdominal aorta for the direct measurement of the arterial blood pressure.

The ECG was traced with subcutaneous insertion electrodes.

During the preparation of the animal and during the entire test period the rats were fixed on an electrically heated and thermostated operating table.

Procedure

The test substances were always introduced by intravenous injection, with an injection volume, per injection, of 1 ml/kg body weight. In intervals of 10 min each, doses increasing from 0.01 to 30 mg of the test substances were intravenously injected. In this way dose effect curves for the measured parameters for the investigated substances were obtained.

From the measured data, using a regression calculation, equipotent doses for the positively inotropic effect $\Delta(dp/dt)_{60}$ were calculated. In addition, as criterion for the effectiveness of the substances, the maximum effect obtained maximal increase of $(dp/dt)_{60}$ and its corresponding dose were determined. The table that follows shows the equipotent

| Table of Results | | | |
|---|---|---|---|
| | $DE_{1.5}$ mHg/sec | $W_{max}$ | |
| Substance | [mg/kg i.v.] | [mHg/sec] | [mg/kg i.v.] |
| Ex. 3A | 0.37 | 4.2 | 10 |
| Ex. 6A | 1.03 | 2.8 | 10 |
| Ref. 1 | 1.17 | 3.5 | 10 |
| Ref. 2 | >>3.0 | 0.6 | 3.0 | doses ($DE_{1.5}$=the dose in mg/kg that leads to an increase of $(dp/dt)_{60}$ of 1.5 mHg/sec) and the maximal effectiveness ($W_{max}$=the maximal increase of $(dp/dt)_{60}$.

In brackets the corresponding dose is shown.

The values show, that the substances of Ex. 3A and 6A are more potent than the substances, used as standards (Ref. 1 and Ref. 2).

Ref. 1: 3-Amino-6-methyl-5-phenyl-2(1H)-pyrridinone-methane-sulfonate

Ref. 2: 3,4-Dihydro-6-[4-(3,4-dimethoxybenzoyl)-1-piperazinyl]-2(1H)-quinolinone It will be understood that the specification and examples are illustrative but not limitative of the present invention and that other embodiments within the spirit and scope of the invention wil suggest themselves to those skilled in the art.

What is claimed is:

1. A compound or tautomer thereof, of the formula:

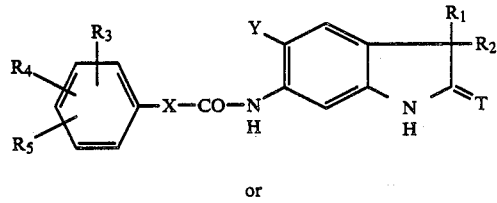

or

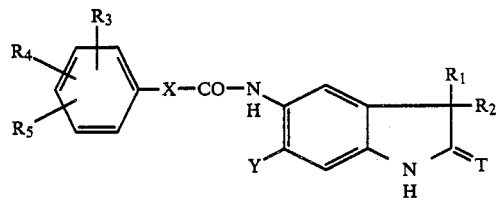

wherein $R_1$ is hydrogen, $C_1$–$C_6$ alkyl, $C_2$–$C_6$ alkenyl or $C_3$–$C_7$ cycloalkyl;

$R_2$ is hydrogen, cyano, $C_1$–$C_6$ alkyl, $C_2$–$C_6$ alkenyl, or a carbonyl group substituted by hydroxyl, $C_1$–$C_6$ alkyl, $C_1$–$C_6$ alkoxy, amino, $C_1$–$C_6$ alkyamino, $C_2$–$C_{12}$ dialkylamino or hydrazino, or $R_2$ and $R_1$ together with the carbon to which they are attached form a $C_3$–$C_7$ spirocycloalkyl ring, or $R_1$ and $R_2$ together form a $C_3$–$C_7$ alkylidene or a $C_3$–$C_7$ cycloalkylidene radical;

$R_3$, $R_4$ and $R_5$, which can be the same or different, each represent hydrogen; $C_1$–$C_5$ alkanesulphonyloxy; trifluoromethanesulphonyloxy; $C_1$–$C_5$ alkanesulphonylamino; trifluoromethanesulphonylamino; N-alkyl-alkanesulphonylamino with 1 to 5 carbon atoms in each alkyl moiety; $C_1$–$C_5$ N-alkyl-trifluoromethanesulphonylamino; $C_1$–$C_5$ alkylsulphenylmethyl; $C_1$–$C_5$ alkylsulphinylmethyl; $C_1$–$C_5$ alkylsulphonylmethyl; carbonyl substituted by hydroxyl, $C_1$–$C_5$ alkoxy, amino, $C_1$–$C_5$ alkylamino or $C_2$–$C_{10}$ dialkylamino; sulphonyl substituted by amino, $C_1$–$C_5$ alkylamino, $C_2-C_{10}$ dialkylamino, morpholino, pyrrolidino, piperidino or hexamethyleneimino; $C_1-C_5$ alkylcarbonylamino, aminocarbonylamino, $C_1-C_5$ alkylaminocarbonylamino radical, $C_1-C_5$ alkylthio, $C_1-C_5$ alkylsuphinyl or $C_1-C_5$ alkylsulphonyl radical, a nitro, halogen, amino, hydroxyl, $C_1-C_5$ alkyl, trifluoromethyl, $C_1-C_5$ alkoxy, $C_1-C_5$ alkenyloxy, $C_2-C_5$ alkynyloxy, cyano($C_1-C_5$)alkoxy, carboxyl-($C_1-C_5$)alkoxy, ($C_1-C_5$)alkoxycarbonyl($C_1-C_5$)alkoxy, $C_2-C_{10}$ dialkylamino, 1-imidazolyl or cyano group;

X is a valency bond, $C_1-C_4$ alkylene or vinylene

Y is hydrogen, amino or nitro, and

T is an oxygen or a physiologically acceptable salt thereof with an inorganic or organic acid.

2. The compound or tautomer thereof, of claim 1 wherein $R_1$ is a hydrogen atom, methyl or ethyl radical and $R_2$ is hydrogen, cyano, methyl, ethyl, isopropyl, methylcarbonyl, methoxycarbonyl, ethoxycarbonyl, aminocarbonyl or hydrazinocarbonyl group or $R_1$ and $R_2$ form together with the carbon atom to which they are attached a spirocyclopentyl ring or $R_1$ and $R_2$ together form an isopropylidene radical, and $R_3$ is hydrogen, a methyl, trifluoromethyl, cyano, methylsulfenylmethyl, methylsulfinylmethyl, methylsulfonylmethyl, hydroxy, methoxy, amino, nitro, dimethylamino, chloro, aminocarbonylamino, N-methylaminocarbonylamino, methylcarbonylamino, methylsulfonylamino, N-methyl-methylsulfonylamino, cyanomethoxy, methoxycarbonylmethoxy, propargyloxy, methylsulfonyloxy, ethylsulfonyloxy, trifluoromethylsulfonyloxy, methylsulfinyl, aminosulfonyl, methylaminosulfonyl, n-butylaminosulfonyl, N,N-dimethylaminosulfonyl, morpholinosulfonyl, methylsulfenyl, methylsulfonyl, 1-imidazolyl, carboxy, ethoxycarbonyl or aminocarbonyl group;

$R_4$ is a hydrogen atom, a chloro, methoxy or nitro group;

$R_5$ is a hydrogen atom or methoxy group;

X is a valency bond, $C_1-C_2$ alkylene or vinylene;

Y is hydrogen, amino or nitro, and

T is an oxygen atom; or a physiologically acceptable salt thereof.

3. The compound of tautomer thereof of claim 1 wherein $R_1$ is hydrogen, methyl or ethyl, $R_2$ is methyl, ethyl, isopropyl or ethoxycarbonyl or $R_1$ and $R_2$ together with the carbon atom to which they are attached form a spirocyclopentyl ring $R_3$ is a hydrogen atom, a methyl, trifluoromethyl, hydroxy, methoxy, nitro, dimethylamino, amino, chloro, N-methylaminocarbonylamino, methylcarbonylamino, methylsulfonylamino, methylsulfonyl, methylsulfenyl, methylsulfonyloxy, carboxy, ethoxycarbonyl, aminocarbonyl, cyano or 1-imidazolyl group $R_4$ is hydrogen or methoxy group $R_5$ is hydrogen X is a valency bond, $C_1-C_2$ alkylene or vinylene;

Y is hydrogen or nitro;

T is oxygen or a physiologically acceptable salt thereof.

4. The compound or tautomer thereof, of claim 3, wherein $R_1$ is hydrogen, methyl or ethyl, $R_2$ is methyl, ethyl or ethoxy, $R_3$ is a hydrogen atom or a hydroxy, methoxy, methyl, trifluoromethyl, 1-imidazolyl or methylsulfonyl group, $R_4$ is hydrogen or methoxy, $R_5$ is hydrogen or a physiologically acceptable salt thereof.

5. The compound of claim 3 wherein $R_1$ and $R_2$ are the same and are methyl or ethyl.

6. The compound or tautomer thereof, of claim 1 wherein $R_1$ and $R_2$ form a spirocyclopentyl ring.

7. The compound or tautomer thereof, of claim 1, wherein Y is hydrogen.

8. The compound or tautomer thereof of claim 1, wherein Y is nitro.

9. The compound or tautomer thereof of claim 1 wherein X is a valency bond or vinylene.

10. Compound of claim 1, designated 3-ethoxycarbonyl-3-methyl-6-benzoylaminoindolin-2-one.

11. Compound of claim 1, designated 3,3-dimethyl-6-(3-phenylpropenoylamino)indolin-2-one.

12. Compound of claim 1, designated 3,3-dimethyl-6-benzoylamino-indolin-2-one.

13. Compound of claim 1, designated 3,3-dimethyl-6-(2-methoxybenzoylamino)indolin-2-one.

14. Compound of claim 1, designated 3,3-dimethyl-6-(4-methoxybenzoylamino)indolin-2-one.

15. Compound of claim 1, designated 3,3-dimethyl-6-(4-methylbenzoylamino)indolin-2-one.

16. Compound of claim 1, designated 3,3-dimethyl-6-(4-trifluoromethylbenzoylamino)indolin-2-one.

17. Compound of claim 1, designated 3,3-dimethyl-6-(2-methoxy-4-methylsulfonylbenzoylamino)indolin-2-one.

18. Compound of claim 1, designated 6'-(4-methoxybenzoylamino)-spiro(cylopentan-1,3'-indolin)-2'-one.

* * * * *